(12) United States Patent
    Sherwinter

(10) Patent No.: US 9,375,137 B2
(45) Date of Patent: Jun. 28, 2016

(54) GASTRIC BOUGIE/DILATOR WITH INTEGRAL LIGHTED TIP

(71) Applicant: Cook Medical Technologies LLC, Bloomington, IN (US)

(72) Inventor: Danny A. Sherwinter, Brooklyn, NY (US)

(73) Assignee: BRAINCHILD SURGICAL DEVICES LLC, Brooklyn, NY (US)

( * ) Notice: Subject to any disclaimer, the term of this patent is extended or adjusted under 35 U.S.C. 154(b) by 240 days.

(21) Appl. No.: 14/024,491

(22) Filed: Sep. 11, 2013

(65) Prior Publication Data

US 2014/0073858 A1    Mar. 13, 2014

Related U.S. Application Data

(60) Provisional application No. 61/743,729, filed on Sep. 11, 2012.

(51) Int. Cl.
    *A61B 1/06* (2006.01)
    *A61B 17/11* (2006.01)
    (Continued)

(52) U.S. Cl.
    CPC ............. *A61B 1/06* (2013.01); *A61B 17/1114* (2013.01); *A61B 2017/00278* (2013.01); *A61B 2017/00818* (2013.01); *A61B 2017/1135* (2013.01);
    (Continued)

(58) Field of Classification Search
    CPC ................. A61B 1/06; A61B 17/1114; A61B 2019/5204; A61B 2019/521; A61B 2019/5445; A61B 2017/00278; A61B 2017/00818; A61B 2017/1135

USPC ......... 600/109, 113, 114, 129, 199, 204, 206, 600/249; 606/2, 10, 11, 191
See application file for complete search history.

(56) References Cited

U.S. PATENT DOCUMENTS 5,179,938 A * 1/1993 Lonky ........................... 600/223
5,226,429 A   7/1993 Kuzmak
(Continued)

FOREIGN PATENT DOCUMENTS

CN    201235137 Y    5/2009
WO    2009097585 A1  8/2009

OTHER PUBLICATIONS

Derwent 2009-J70906, cf. Shi M et al., CN 201235137Y, China, May 2009.*

(Continued)

*Primary Examiner* — Pedro Philogene
*Assistant Examiner* — David C Comstock
(74) *Attorney, Agent, or Firm* — Marsh Fischmann & Breyfogle, LLP; Daniel J. Sherwinter

(57) ABSTRACT

The invention is a lighted gastric surgical bougie which includes an integral light source disposed at the distal end that, when activated, is detectable through the gastric wall of a patient during gastric surgery. The light source enables a surgeon to identify the location of the bougie within the patient. The light source may include at least one LED integrally disposed at the distal end. Optionally, a second LED is integrally disposed on the main body a longitudinal distance away from the at least one LED at the distal end. The second LED may be disposed near the tapered region so that a surgeon can readily identify the location of the tapered region with respect to the patient's anatomy. Preferably, the second LED at the proximal portion of the tapered region is visibly different than the at least one LED. Alternatively, the light source is chemiluminescent.

20 Claims, 3 Drawing Sheets

(51) Int. Cl.
  *A61M 29/00*    (2006.01)
  *A61B 19/00*    (2006.01)
  *A61B 17/00*    (2006.01)

(52) U.S. Cl.
  CPC ... *A61B2019/521* (2013.01); *A61B 2019/5204* (2013.01); *A61B 2019/5445* (2013.01); *A61B 2090/3945* (2016.02); *A61M 29/00* (2013.01)

(56) References Cited

U.S. PATENT DOCUMENTS

| | | | |
|---|---|---|---|
| 5,400,770 | A | 3/1995 | Nakao et al. |
| 5,624,432 | A | 4/1997 | Angelchik |
| 5,718,666 | A | 2/1998 | Alarcon |
| 5,766,202 | A | 6/1998 | Jones et al. |
| 7,226,429 | B2 | 6/2007 | Tullis |
| 7,794,386 | B2 | 9/2010 | Brooks |
| 7,901,353 | B2 | 3/2011 | Vayser et al. |
| 8,226,671 | B2 | 7/2012 | Laufer |
| 2003/0093088 | A1 | 5/2003 | Long et al. |
| 2005/0090711 | A1 | 4/2005 | Fuchs et al. |
| 2005/0096750 | A1 | 5/2005 | Kagan et al. |
| 2008/0017195 | A1* | 1/2008 | Yoshida ............... 128/200.26 |
| 2009/0143639 | A1 | 6/2009 | Stark |
| 2009/0318757 | A1 | 12/2009 | Singh |
| 2010/0081883 | A1 | 4/2010 | Murray et al. |
| 2012/0116161 | A1 | 5/2012 | Nieman et al. |
| 2012/0123463 | A1 | 5/2012 | Jacobs |
| 2012/0191123 | A1 | 7/2012 | Brister et al. |
| 2013/0006166 | A1 | 1/2013 | Klein et al. |
| 2013/0131440 | A1 | 5/2013 | Gabriel |

OTHER PUBLICATIONS

PCT Appln. No. PCT/US2013/059307, International Search Report and Written Opinion dated Dec. 18, 2013.

* cited by examiner

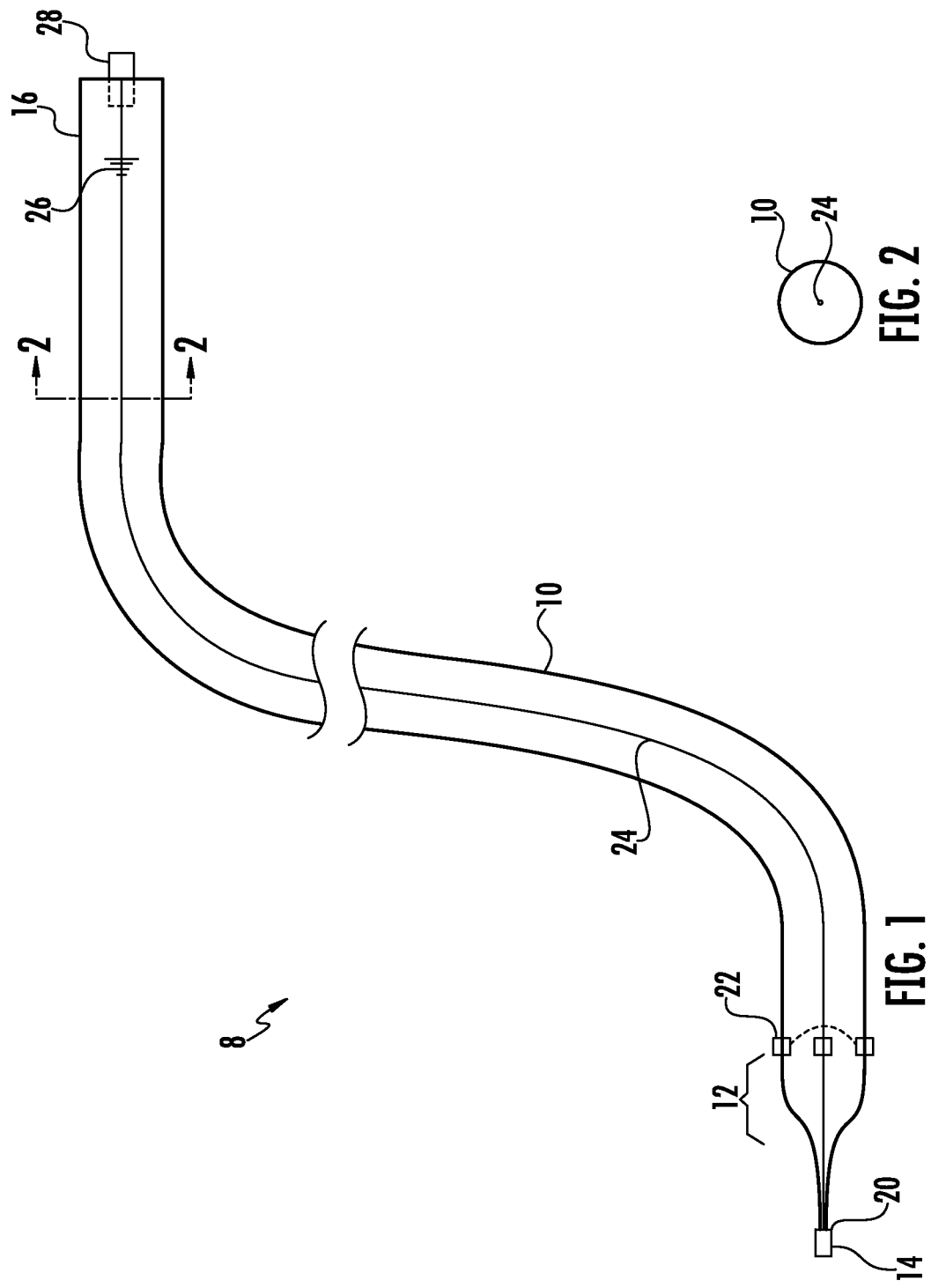

GASTRIC BOUGIE/DILATOR WITH INTEGRAL LIGHTED TIP

RELATED APPLICATIONS

Priority is claimed from U.S. Provisional Patent Application No. 61/743,729 filed Sep. 11, 2012, entitled "Gastric Bougie/Dilator with Lighted Tip", the teachings of which are incorporated by reference herein.

BACKGROUND OF THE INVENTION

1. Field of the Invention

The invention is directed to surgical devices. More specifically the invention is directed to gastric surgical devices such as bougies or dilators with improved location and placement ability.

2. Description of Related Art

Obesity is a common and growing problem in the United States and the rest of the world. Owing to poor diet, unthoughtful community planning that de-emphasizes walking and outdoor spaces, and plenty of sedentary distractions, people are becoming fatter in epidemic proportions.

One vector to combat the obesity epidemic is bariatric or weight loss surgery. During such surgery in general, portions of the gastrointestinal tract are either removed, bypassed, or constricted to prevent excessive amounts of food from being ingested by the patient afterwards. Weight loss is extremely common thereafter.

During gastric sleeve resections for weight loss (vertical sleeve gastrectomy, VSG) and other operations involving the esophagus and stomach, there is a need for placement of a bougie/dilator, a slender, flexible, hollow or solid, cylindrical instrument for introduction into a tubular organ, usually for calibrating or dilating constricted areas. The bougie is placed down via the mouth and across the esophagus and/or stomach or small bowel. The purpose of this device is to act to dilate strictures and/or help delineate the borders of the stomach/esophagus for resection. Standard sizes include 34 French to 40 French but a myriad of diameters can at times be needed. The bougie/dilator can have a blunt tip or a tapered tip and can be wire guided or placed blindly. The device can be constructed out of any biocompatible material such as medical grade plastic silicon or similar material which has the appropriate degree of rigidness and flexibility to accomplish this purpose.

During placement of the bougie/dilator there is a vital need to know and identify the location of the distal-most aspect of the dilator tip. In the case of a VSG procedure the bougie dilator must be maintained in the proper position throughout to ensure adequate diameter of the sleeve. A sleeve made too small by, for example, slippage of the bougie out of place can be devastating causing gastric obstruction sepsis and death. Since the bougie/dilator is contained within the lumen of the stomach and the wall of this organ is opaque there is a need for some method to identify the location of the tip and thereby ensure that it has not slipped back or moved.

In addition, there are other gastric surgical procedures that currently employ a bougie. For example, when a patient has a naturally occurring improper gastric constriction or obstruction, a bougie may be employed to dilate the constriction or open the obstruction. In these cases as well, knowledge of the precise location of the bougie, especially the tip of the bougie, with respect to the anatomy of the patient, is highly desirable.

SUMMARY OF THE INVENTION

The invention is a lighted gastric surgical bougie. The inventive bougie includes a flexible substantially cylindrical main body having a proximal end and a distal end. An integral light source is disposed at the distal end that, when activated, is detectable through the gastric wall of a patient during gastric surgery. The light source enables a surgeon to identify the location of the distal end of the bougie with respect to the patient's anatomy.

Preferably, the light source is detectable by a laparoscopic camera inserted into the body of the patient. The light source preferably emits at least one of visible, IR, or UV light. The preferred embodiment of the inventive bougie is disposable.

In one embodiment, the light source includes at least one LED integrally disposed at the distal end. Preferably, a power source is disposed within the main body in electrical communication with the at least one LED. Optionally, a second LED is integrally disposed on the main body a longitudinal distance away from the at least one LED at the distal end. The main body preferably further includes a tapered region substantially adjacent to the distal end, and the second LED is disposed substantially at a proximal portion of the tapered region so that a surgeon can readily identify the location of the tapered region with respect to the patient's anatomy. Preferably, the second LED at the proximal portion of the tapered region is visibly different than the at least one LED at the distal tip. More than two LEDs or light sources may be employed, e.g., along the uniform main body in addition to those at the tip and tapered regions. Different regions may optionally be provided with visually different light sources, e.g., different colors, blinking versus steady, different blink rates, and the like.

In an alternative embodiment, instead of a power source and an LED, the light source of the inventive bougie includes a chemiluminescent source. More specifically, the chemiluminescent source may further include a first chemical contained in a breakable inner container disposed within the distal tip of the main body and a second chemical surrounding the inner container but contained within a pocket within the distal tip of the main body. Upon flexing of the distal tip of the main body, the inner container breaks, the first and second chemicals mix, and light is produced via chemiluminescence. Preferably, the first and second chemicals are biocompatible.

In either lighting option, the main body may be either substantially longitundinally straight or slightly longitundinally curved in its unflexed configuration.

The inventive bougie attaches a light to the tip of the bougie dilator detectable by a laparoscopic camera system through the visceral wall which will indicate the location of the tip of the bougie dilator.

There are a number of ways of attaching an indicator light to the tip of the bougie/dilator. The light generated can be infrared ultraviolet or be contained within the visible spectrum. The light can be continuous or pulsed and in a myriad of different colors as to be easily visible within the abdominal cavity.

In the preferred embodiment, an LED or similar light source is provided integral with and encased within the tip of the bougie dilator, and a power source and an actuating device contained within the body of the bougie/dilator. The actuating device may be an on-off switch accessible from the proximal end of the bougie, or it may simply be a pull tab which, when installed, blocks current from flowing to the LED, the removal of which enables current to flow. A non-powered chemiluminescent bougie tip may also be provided.

The bougie dilator is preferably disposable but in an alternative embodiment be reusable if the light and/or power sources were renewable or replaceable.

BRIEF DESCRIPTION OF THE DRAWINGS

FIG. 1 is a side schematic of a bougie in accordance with the invention.

FIG. 2 is a sectional view of the bougie of FIG. 1 taken along line II-II.

DETAILED DESCRIPTION OF THE INVENTION AND DRAWINGS

Figure 3A:
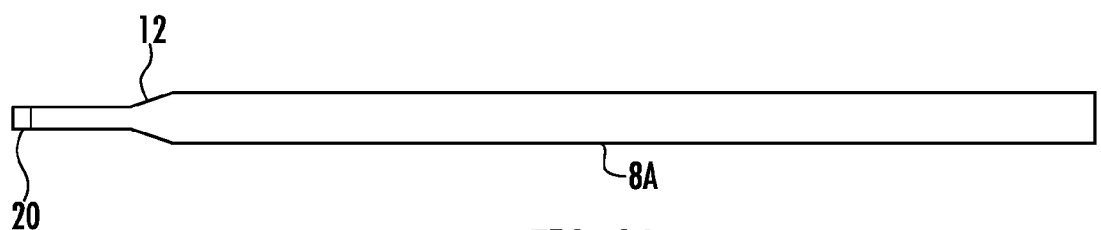
FIGS. 3A-B are side schematics of two embodiments of a bougie in accordance with the invention in their unflexed configuration.

Description will now be given with reference to the attached FIGS. 1-4. It should be understood that these figures are exemplary in nature and in no way serve to limit the scope of the invention, which is defined by the claims appearing hereinbelow.

FIG. 1 is a side schematic of a bougie 8 in accordance with the invention. Bougie 8 includes a main body 10 which is substantially cylindrical in shape, either solid or hollow, and essentially uniform in diameter. Main body 10 must be sufficiently flexible to be able to bend along the GI tract as it is inserted therealong but be stiff enough to maintain its shape and not collapse. Bougie 8 has a distal end 14 and a proximal end 16. Just behind distal end 14 is a tapered section 12 in which the diameter of bougie 8 decreases from its uniform section of main body 10 to the narrower section of distal end 14.

Disposed at or near the very end of distal end 14 is integral light source 20 which, in FIG. 1, is one or more light emitting diodes (LEDs). Electrical connection 24 is formed or disposed within main body 10 and electrically connects power source 26 (e.g., a battery) to LED 20. Electrical connection 24 may take the form of wiring, or a section of electrically conductive polymer, or the like. As shown in FIG. 2, connection is preferably centrally located within main body 10, however it need not be so located and may be instead located anywhere radially therein that is convenient to manufacture while remaining insulated from the patient's body. Power supply 26 is shown in FIG. 1 as being disposed close to the proximal end 16 of bougie 8, however it may be disposed at any convenient location within main body 10. The purpose of light source/LED 20 is to enable the definitive and easy location of bougie within a patient during gastric surgery.

Optionally, to assist in the location of bougie 8, one or more secondary light source(s)/LEDs 22 may be provided proximal to LED 20 at or near the proximal portion of tapered section 12. Preferably, LED(s) 22 might be made visually distinct from LED(s) 20. For example, LEDs 22 might be a different color than LEDs 20, or one may be steady and the other may blink, or any other known or to be developed ways to distinguish LEDs or similar light sources visually.

Bougie 8 is preferably provided with power controller 28 at the proximal end of main body 10. Power controller 28 is provided to enable the surgeon to activate power source 26 and thus turn on light source 20 and/or 22. In one embodiment, power controller 28 is a switch, e.g., a toggle switch or the like. In another embodiment, to reduce manufacturing costs, power controller 28 may simply take the form of a pull-tab that blocks the flow of current from power supply 26 to LEDs 20 and/or 22. Removing the pull tab completes the circuit, and current flows to the LEDs/light sources. This latter embodiment ensures that the batteries of bougie 8 are fresh and will successfully power the LEDs/light sources upon removal from the sterilized packaging even if stored therein for an extended period of time.

This embodiment is preferably completely self-contained and entirely disposable after a use. The preferred embodiment has one or more LEDs with one or more button batteries imbedded in the bougie, either with an on/off switch or a pull tab. This type of embodiment would not only be less expensive to manufacture than a fiber optic version but would also be easier to manage from a materials management standpoint because it would be one package sterile to open per case.

Figure 3B:
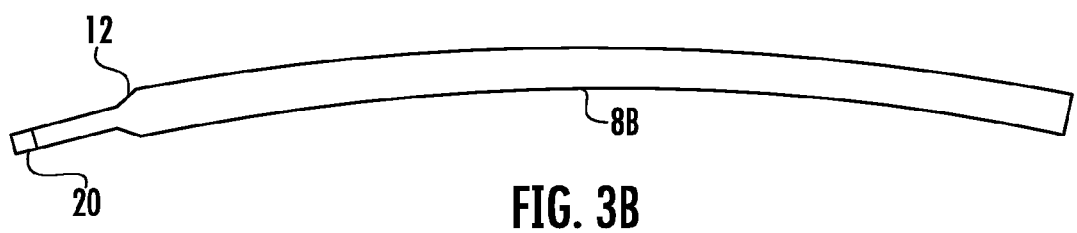

FIG. 3 depicts two different shapes of bougie 8. In FIG. 3A, bougie 8A is substantially straight when in an unflexed configuration. In FIG. 3B, bougie 8B is slightly curved or arced to better enable its insertion into and travel along the GI tract. (The S-shape of the bougie of FIG. 1 schematically represents the bougie being deployed within the sinuous GI tract.)

Figure 4:
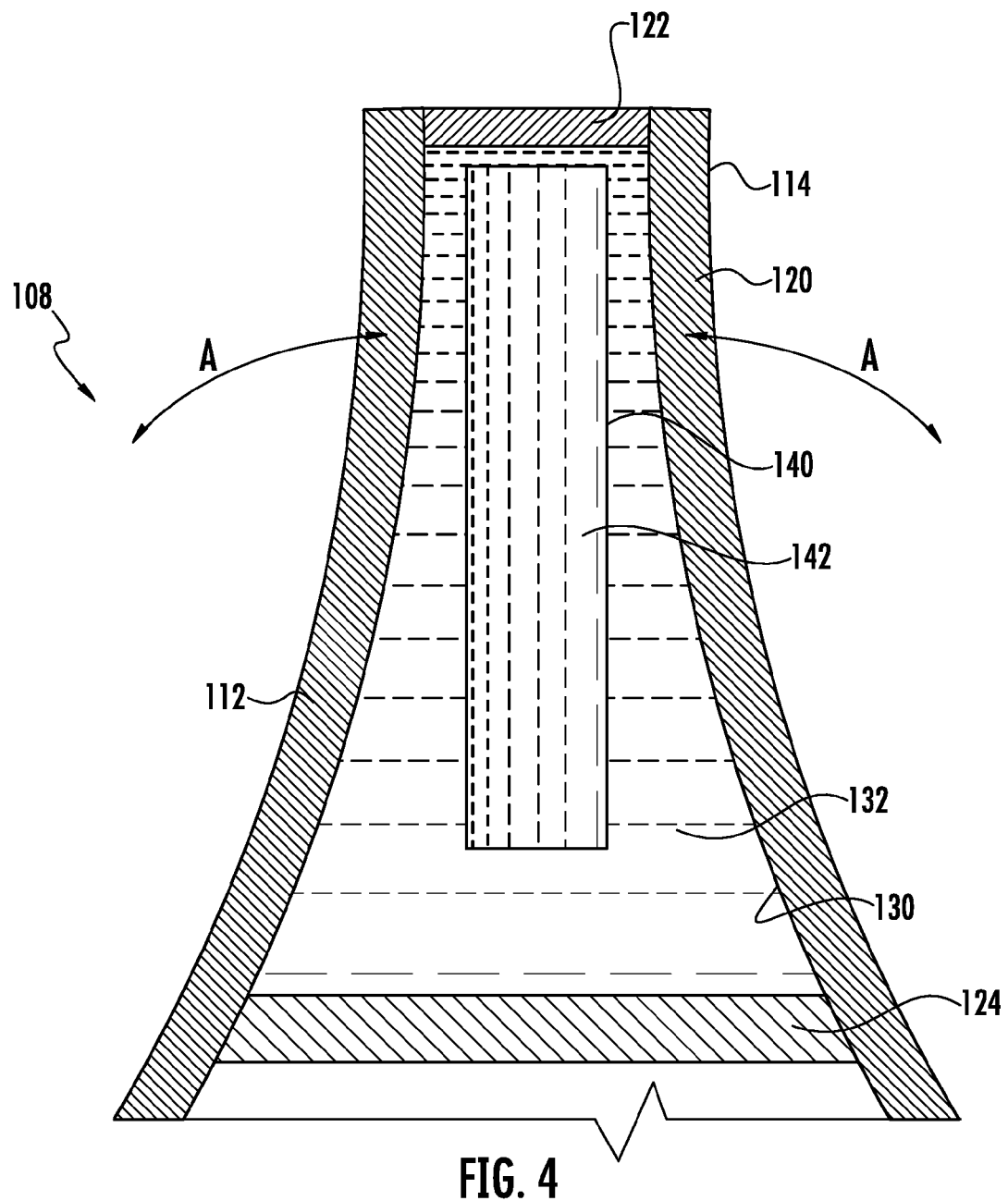
FIG. 4 is a sectional view of the distal tip of an alternate embodiment of a bougie in accordance with the invention.

FIG. 4 depicts the distal tip 114 of an alternative embodiment of the invention in bougie 108. Here, instead of providing a powered light source like an LED, light source 120 is chemiluminescent and needs no power to be activated. The side walls of distal tip 114 are made from a light-transmissible material. The side walls, distal wall 122, and proximal wall 124 together define an outer chamber or pocket 130 in which a first chemical 132 is provided. Disposed within outer chamber 130 is an inner container 140 housing a second chemical 142. The side walls of distal tip 114 are made to be resilient and flexible as the rest of bougie 108, however inner container is designed to be significantly more fragile and breakable. To wit, when a lateral force is applied across distal tip 114 in the direction of arrows A (e.g., the user bends distal tip 114 with his hands), inner container 140 will snap or break, releasing chemical 142 which then mixes with chemical 140. When the two chemicals mix, a reaction occurs that releases light. Many such chemicals are generally known; it is preferred that the invention use chemicals that are biocompatible to reduce the chances of toxic exposure to the patient should the outer chamber 130 somehow be compromised.

The provision of a simple yet fully integrated light source at the distal end of a bougie has not been proposed. Some prior art bougies have made use of optical fibers to conduct light from an external light source to the tip or other location. A fiber optic version is more complex and more costly to make and requires an external light source. Additionally, up until recently, there were limited if any applications where one would need a bougie and the need to visualize it through the gastric wall Vertical sleeve gastrectomy (VSG) is a relatively new procedure in bariatric surgery and one that is perfect for the invention. Additionally, a new technique for performing gastric bypass (RYGB) also requires a bougie, while the previous techniques never needed a bougie.

In operation, the device is implemented as follows. The device comes presterilized in sterile packaging for single use. It comes preloaded with batteries with a small plastic tab preventing contact until the package is opened and ready for use and the tab is manually removed. Alternatively, the chemiluminescent embodiment comes with the first and second chemicals completely separated but ready to be mixed by the application of force across the distal tip of the device. Since the device is disposable it does not require subsequent or additional sterilization or maintenance. It is entirely solid state and integral without the need to purchase capital equipment, an external light source, or delicate optical fibers.

Vertical sleeve gastrectomy (VSG). The procedure begins by first mobilizing the greater curve of the stomach. Prior to stapling and dividing the stomach, the device is advanced via the mouth. Even though the gastric wall is opaque and the device itself is not visible through the gastric wall, the lighted tip is visible, and it is thus possible to observe the progress of the device as it is passed into the correct position. Since the tip can be observed, the surgeon can appropriately direct the technician placing the device and thereby get the device placed more quickly (i.e., with fewer placement iterations) and more safely (i.e., with fewer or no inadvertent and potentially damaging encounters with neighboring delicate anatomical structures). This is in contrast to a non-lighted bougie which is placed blindly. Using the tip light (e.g., red) as a guide, the device is advanced until it comes to rest in the antrum of the stomach. The stapler would then be fired in a vertical fashion along the uniform side of the device thus standardizing the diameter of the sleeve. Once the stapler is fired along the uniform shaft of the device from the antrum to the esophagus and the stomach disconnected, the device is removed and discarded. The position of the device can be confirmed at all times throughout the stapling procedure and it can be ensured as to not having slipped back by observing the lighted tip in the gastric antrum. This is in contrast to a non-lighted bougie which is placed blindly and can injure the other organs (e.g., esophagus, stomach, pharynx), is difficult to place and may require multiple passes until it finds itself in the right place and more importantly can easily slip back unnoticed during the procedure. This is such an insidious problem because if the surgeon fails to notice that the bougie is no longer directing his staple line formation and he continues stapling, he will either make the sleeve too big and thus useless or narrow the lumen and thus cause a catastrophic obstruction of the stomach.

An additional manifestation of the device would be to add visually or otherwise detectably different light sources along the shaft to enable confirmation of the locations of the different sections of the device which have varying diameters/thicknesses (thin distal tip, tapered section, uniform diameter main body proximal thereto). Such a light pattern will confirm that the appropriately diameter portion of the device is positioned in such a way as to adequately size the sleeve which is to be created. Additionally, as mentioned above, the only area it is safe to staple is along the uniformly diametered main body. By providing lights along the entire device to delineate the various sections, the risk of improperly stapling the stomach at an area where the device is still tapered is minimized. Different colored LEDs can be used to highlight each area. For example a red LED may be employed at the tip, a blue LED at the taper, and then green at the beginning of the uniform shaft or all along the uniform shafted area. Any other colors, combinations, steady versus blinking, and the like may be employed. This also contrasts the invention with fiber optic concepts which use only a single color light and yet are more complicated to make and use owing to the additional sterilization requirements and the need for an external light source, among other reasons. The simplest embodiment of the invention, of course, would be to employ only one LED or similar light source at the distal tip, which would still allow the surgeon to follow the progress of the bougie and keep track of it throughout the stapling procedure.

Roux en Y gastric bypass (RYGB). The procedure begins by dividing the stomach to create a 15-30 cc pouch out of the proximal stomach. An appropriate limb of jejunum is then brought up to the gastric pouch and connected via a linear stapler. This leaves a common defect in both the stomach pouch and the jejunum which must be closed. The standard technique is to suture this closed. In closing this defect, great care must be taken in order to not narrow the connection (anastomosis) between these two structures. At this point, prior to suturing the common defect closed, the device will be passed via the mouth into the stomach. Using the lighted tip as a guide it is then advanced into the jejunum and across the anastomosis. Using the device as a sizer, the defect is then sutured closed. The lighted tip and/or shaft (see above regarding varied LED colors, display patterns, etc.) acts to confirm throughout the suturing process that the device is in the proper position and is appropriately sizing the anastomosis. By contrast, if a non-lighted bougie was used and it inadvertently slipped back into the stomach or esophagus during suturing, which could easily happen because the stomach and jejunal walls are opaque, the surgeon would have no way to know that this had happened and would thus likely sew the anastomosis closed causing a catastrophic obstruction.

Bougies come in many different diameters and lengths, and the instant invention is no exception. For example, the inventive bougie may be provided in 36 French diameter at a length of 70 cm, however any practical length and diameter may be employed.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. A lighted gastric surgical bougie, comprising:
a flexible substantially cylindrical main body having a proximal end and a distal end; and
an integral light source disposed at said distal end and narrowest point of a tapered region being narrower than said main body that, when activated, is detectable through the gastric wall of a patient during gastric surgery, wherein said light source enables a surgeon to identify the location of said distal end of said bougie with respect to the patient's anatomy.

2. A lighted gastric surgical bougie according to claim 1, said light source comprises at least one LED integrally disposed at said distal end.

3. A lighted gastric surgical bougie according to claim 2, further comprising a power source disposed within said main body in electrical communication with said at least one LED within said proximal and bendable end of said main body next to a bent region of the main body.

4. A lighted gastric surgical bougie according to claim 2, further comprising a second LED integrally disposed on said main body at a second position a longitudinal distance away from said at least one LED at said distal end wherein said second LED enables the surgeon to identify the location of said second position on the main body with respect to the patient's anatomy.

5. A lighted gastric surgical bougie according to claim 4, said main body further comprising said tapered region substantially adjacent to said distal end, said tapered region having a first diameter of said main body and decreasing to a narrower section at a distal end opposite an end adjacent to said main body, wherein said second LED is disposed substantially at a proximal portion of said tapered region so that a surgeon can readily identify the location of said tapered region with respect to the patient's anatomy.

6. A lighted gastric surgical bougie according to claim 5, wherein said second LED at said proximal portion of said tapered region is visibly different in blink rate than said at least one LED.

7. A lighted gastric surgical bougie according to claim 1, wherein said light source is detected by a laparoscopic camera inserted into the body of the patient.

8. A lighted gastric surgical bougie according to claim 1, wherein said light sources, in combination, emits at least two of visible, IR, or UV light.

9. A lighted gastric surgical bougie according to claim 8, wherein said light source emits IR light or UV light.

10. A lighted gastric surgical bougie according to claim 1, wherein said bougie is disposable.

11. A lighted gastric surgical bougie according to claim 1, said light source comprises a chemiluminescent source.

12. A lighted gastric surgical bougie according to claim 11, said chemiluminescent source further comprising:
   a first chemical contained in a breakable inner container disposed within said distal tip of said main body; and
   a second chemical surrounding said inner container but contained within a pocket within said distal tip of said main body, wherein upon flexing of said distal tip of said main body, said inner container breaks, said first and second chemicals mix, and light is produced via chemiluminescence.

13. A lighted gastric surgical bougie according to claim 12, wherein said first and second chemicals are biocompatible.

14. A lighted gastric surgical bougie according to claim 1, wherein said main body is substantially longitudinally straight in its unflexed configuration.

15. A lighted gastric surgical bougie according to claim 1, wherein said main body is slightly longitudinally curved in its unflexed configuration.

16. A lighted gastric surgical bougie according to claim 1, further comprising:
   a plurality of different sections of said bougie each having a different diameter from the other of said sections, including a main body having a widest diameter and tapered tip having a gradually narrowing diameter; and
   at least one light source disposed in each of said sections, including at least one said light source on said main body and at least one said light source at a distal end of said tapered tip to indicate to the surgeon the location of each of said sections with respect to patient anatomy during a procedure.

17. A lighted gastric surgical bougie according to claim 16, wherein each of said light sources in each of said sections is detectably different from the other of said light sources.

18. A lighted gastric surgical bougie according to claim 1, wherein said flexible substantially cylindrical main body is formed from a plastic material.

19. A lighted gastric surgical bougie, comprising:
   a flexible substantially cylindrical main body formed from a plastic material having a proximal end and a distal end; and
   an integral first light source disposed at said distal end that, when activated, is detectable through the gastric wall of a patient during gastric surgery, wherein said first light source enables a surgeon to identify the location of said distal end of said bougie with respect to the patient's anatomy, and
   a second light source integrally disposed on said main body a second position on the main body a longitudinal distance away from said at least first light source at said distal end, wherein said second light source enables the surgeon to identify the location of said second position on the main body with respect to the patient's anatomy.

20. A lighted gastric surgical bougie according to claim 19, said light source comprises at least one LED integrally disposed at said distal end.

\* \* \* \* \*